United States Patent [19]

Stinson

[11] Patent Number: 5,433,738

[45] Date of Patent: Jul. 18, 1995

[54] METHOD FOR IRRADIATING CELLS

[76] Inventor: Randy L. Stinson, 42 Glen Way, Baltimore, Md. 21236

[21] Appl. No.: 186,239

[22] Filed: Jan. 25, 1994

Related U.S. Application Data

[60] Continuation of Ser. No. 948,420, Sep. 22, 1992, abandoned, which is a division of Ser. No. 378,994, Jul. 12, 1989, Pat. No. 5,150,705.

[51] Int. Cl.$^6$ .............................................. A61N 5/06
[52] U.S. Cl. ........................................ 607/92; 604/4; 607/94; 422/24; 422/44; 250/435
[58] Field of Search ............................. 128/395–398, 128/480; 607/88–94; 604/4; 250/432 R, 455.1, 435, 436, 438, 43, 437; 422/372, 24, 44; 435/284

[56] References Cited

U.S. PATENT DOCUMENTS

| | | | |
|---|---|---|---|
| 1,079,503 | 11/1913 | Linker | 250/436 |
| 1,435,192 | 11/1922 | Anderson | 128/395 |
| 1,681,538 | 8/1928 | Hoffmann . | |
| 1,969,655 | 8/1934 | Mailey . | |
| 2,309,124 | 1/1943 | Knott | 250/48 |
| 2,340,890 | 2/1944 | Lang et al. . | |
| 2,501,290 | 3/1950 | Peguignet | 250/426 |
| 3,551,091 | 12/1970 | Veloz . | |
| 3,786,250 | 1/1974 | Huhn . | |
| 3,894,236 | 7/1975 | Hazelrigg | 250/435 |
| 3,927,325 | 12/1975 | Hungate et al. . | |
| 4,008,045 | 2/1977 | Free | 422/24 |
| 4,065,264 | 12/1977 | Lewin | 128/399 |
| 4,156,652 | 5/1979 | Wiest | 250/438 |
| 4,201,916 | 5/1980 | Ellner . | |
| 4,613,322 | 9/1986 | Edelson | 128/395 |
| 4,621,195 | 11/1986 | Larsson . | |
| 4,647,539 | 3/1987 | Bach . | |
| 4,676,896 | 6/1987 | Norton . | |
| 4,694,179 | 9/1987 | Lew | 250/436 |
| 4,769,131 | 9/1988 | Noll et al. | 250/438 |
| 4,798,702 | 1/1989 | Tucker | 250/438 |
| 4,904,874 | 2/1990 | Ellner | 250/436 |

FOREIGN PATENT DOCUMENTS

| | | |
|---|---|---|
| 282210 | 2/1965 | Australia . |
| 67782/74 | 4/1974 | Australia . |
| 33714/84 | 4/1985 | Australia . |
| 0138489 | 4/1985 | European Pat. Off. . |
| 1447380 | 12/1988 | U.S.S.R. ............... 129/395 |

OTHER PUBLICATIONS

"Pancreatic Islet Transplantation: Immuno-alteration with Ultraviolet Irradiation" Mark A. Hardy, M.D., Henry T. Lau, N.D., Collin Weber, M.D. and Keith Reemtsma, M.D. World Journal of Surgery (vol. 8, No. 2) pp. 207–213.

"Prevention of Platelet Alloimmunization in Dogs With Systemic Cyclosporine and by UV–Irradiation of Cyclosporine-Loading of Donor Platlets" Sherrill J. Slichter, H. Joachim Deeg, and Michael S. Kennedy (vol. 69, No. 2 pp. 414–418.

"Ultraviolet Irradiation of Blood Prevents Transfusion–Induced Sensitization and Marrow Graft Rejection in Dogs" H. Joachim Deeg, Joseph Aprile, Theodore C. Graham, Fredrick R. Appelbaum, and Rainer Storb (vol. 67, No. 2) pp. 537–539.

(List continued on next page.)

Primary Examiner—Mark S. Graham
Attorney, Agent, or Firm—Burns, Doane, Swecker & Mathis

[57] ABSTRACT

An apparatus for irradiating cells with ultraviolet light including an ultraviolet light source and an outer cylinder that surrounds the ultraviolet light source. Hollow tubing is helically wrapped around the outer peripheral surface of the outer cylinder. The hollow tubing is adapted to transport suspended cells over the outer surface of the outer cylinder so that the cells can be irradiated by the ultraviolet light source. An inner cylinder can be positioned inside the outer cylinder, between the ultraviolet light source and the outer cylinder. The apparatus can include an arrangement for ventilating the apparatus during use in order to maintain a substantially constant temperature.

16 Claims, 2 Drawing Sheets

U.S. PATENT DOCUMENTS

"Inability of UV-Irradiated Lymphocytes to Stimulate Allogeneic Cells in Mixed Lymphocyte Culture" K. Lindahl-Kiessling and J. Safwenbert (Int. Arch. Allergy 41: 670–678) 1971.

"The influence of Ultraviolet Irradiation on the Blood Transfusion Effect" James D. Balshi, M.D., John W. Francfort, M.D., and Leonard J. Perloff, M.D. Surgery Aug. 1985 (pp. 243–249) vol. 98, No. 2.

"Prolongation of RaT Islet Allografts With the Use of Ultraviolet Irradiation, Without Immunosuppression" M. A. Hardy, H. Lau and K. Reemtsma Transplantation Proceedings vol. XVI, No. 3 (June) 1984 pp. 865–869.

"Ultraviolet Irradiation in Transplantation Biology" H. Joachim Deeg (vol. 45, No. 5 pp. 845–851 (May 1988).

"Lamp/Filter Systems for Simulation of Solar UV Irradiance Under Reduced Atomosphereic Ozone" Wm. B. Sisson and Martyn M. Caldwell *Photochemistry and Photobiology*, 1975 vol. 21 pp. 453–456.

"Regulation of Antigenic Expression" Charles A. Apffel an John H. Peters J. Theoret. Biol. (1970) vol. 26 pp. 47–49.

Excerpts from *The Photonics Design and Applications Handbook* (1985) pp. 185, 194, 205, 214,215, 217 and 219.

"Light–activated Drugs" by Richard L. Edelson, Scientific American, vol. 259, No. 2, Aug. 1988, pp. 68–75.

"Treatment of Cutaneous T–Cell Lymphoma by Extracorporeal Photochemotherapy" by Richard L. Edelson, et al., Reprinted from the New England Journal of Medicine, Feb. 5, 1987, pp. 297–303, vol. 316, No.6.

"Photopheresis–a new therapeutic power" published by Therakos, Inc., Feb. 1987.

"1985 Photonics Handbook", from publishers of *Spectra Magazine.*

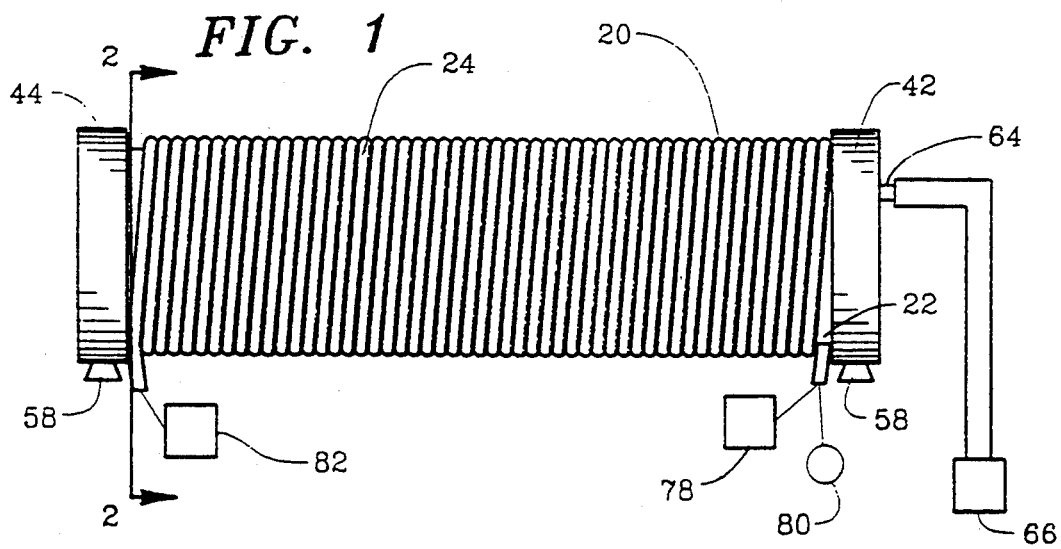
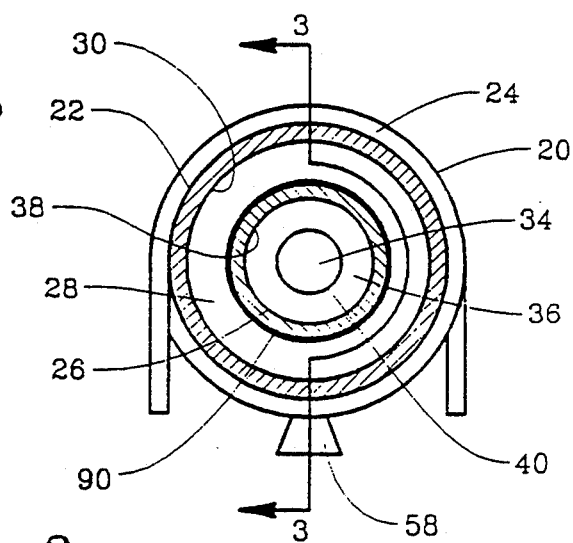
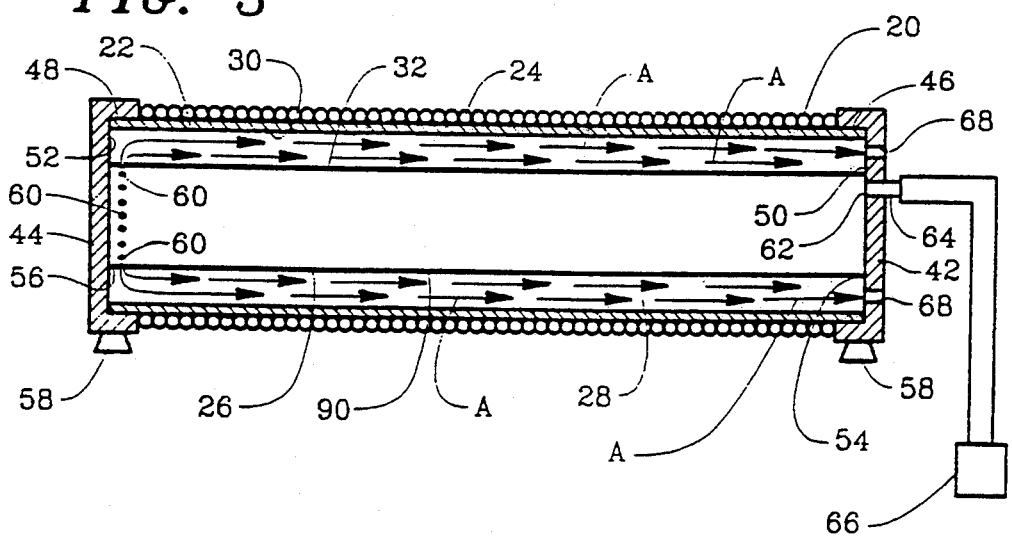

METHOD FOR IRRADIATING CELLS

This application is a continuation of Application Ser. No. 07/948,420, filed Sep. 22, 1992, abandoned which is a divisional application of application Ser. No. 07/378,994, filed Jul. 12, 1989, U.S. Pat. No. 5,150,705.

BACKGROUND OF THE INVENTION

The present invention relates to an apparatus for irradiating fluids. More particularly, the present invention concerns an apparatus for permitting cells to be irradiated by an ultraviolet light source.

The transplantation of cells into an allogeneically different recipient has been researched by several medical investigators in an attempt to treat specific medical diseases and disorders. In order to successfully carry out such a transplantation of cells, it is necessary to immunosuppress antigen expression and/or recognition of the transplanted cells. In that way, the body's natural tendency to reject the transplantation of the allogeneic cells can be overcome.

One generally recognized method for immunosuppressing the antigen expression and recognition of the allogeneic cells is to subject the cells to ultraviolet radiation. The uses of ultraviolet radiation within the context of cellular transplantation are discussed in an article authored by H. Joachim Deeg entitled "Ultraviolet Irradiation in Transplantation Biology," *Transplantation*, Vol. 45, No. 5, pp. 845–851, May 1988.

Several other articles have also been written describing specific methods that have been employed for subjecting transplant cells to ultraviolet radiation. For example, in one method, blood diluted in a phosphate buffer was placed in petri dishes and subjected to ultraviolet light for twenty minutes. The light source emitting the ultraviolet light was positioned at a specified distance from the petri dish. However, not all of the experiments utilizing that method were apparently conducted with the light source positioned at the same distance from the petri dishes. Hardy, M. A., Lau, H. T., Weber, C., Reemtsma, K.: "Pancreatic Islet Transplantation: Immuno-alteration With Ultraviolet Irradiation", *World Journal of Surgery*, Vol. 8, No. 2, pp. 207–213, April 1984. Hardy, M. A., Lau, H., Reemtsma, K.: "Prolongation of Rat Islet Allografts With the Use of Ultraviolet Irradiation, Without Immunosuppression", *Transplantation Proceedings*, Vol. 16, No. 3, pp. 865–869, June 1984.

In another method, platelets were suspended in a solution, placed in an open petri dish to a depth of 1.5 mm and subjected to ultraviolet light irradiation while being continuously shaken. Slichter, S. J., Deeg, H. J., Kennedy, M. S.: "Prevention of Platelet Alloimmunization in Dogs With Systemic Cyclosporine and by UV-Irradiation or Cyclosporine-Loading of Donor Platelets", *Blood*, Vol. 69, No. 2, pp. 414–418, February 1987.

An additional method includes placing whole blood which has been diluted with Waymouth's minimal medium in petri dishes at a layer thickness of 1.5 mm and irradiating the suspension with ultraviolet light for thirty minutes. Deeg, H. J., Aprile, J., Graham, T. C., Appelbaum, F. R., Storb, R.: "Ultraviolet Irradiation of Blood Prevents Transfusion-Induced Sensitization and Marrow Graft Rejection in Dogs", *Blood*, Vol. 67, No. 2, pp. 537–539, February 1986.

Various other articles have been published in addition to those noted above concerning the use of ultraviolet light irradiation on cells. See, for example, Lindahl-Kiessling, K., Säfwenberg, J.: "Inability of UV-Irradiated Lymphocytes to Stimulate Allogeneic Cells in Mixed Lymphocyte Culture", *Int. Arch. Allergy*, Vol. 41, pp. 670–679, 1971; Balsh, J. D., Francfort, J. W., Perloff, L. J.: "The Influence of Ultraviolet Irradiation on the Blood Transfusion Effect", *Surgery*, pp. 243–249, August 1985; Lau, H., Reemtsma, K., Hardy, M. A.: "Prolongation of Rat Islet Allograft Survival by Direct Ultraviolet Irradiation of the Graft", *Science*, Vol. 223, pp. 607–609, Feb. 10, 1984.

It becomes readily apparent from a review of the above articles that the techniques and methods presently employed in ultraviolet light irradiation for transplant and transfusion related procedures suffer from several drawbacks and are susceptible to improvement. In particular, there is no uniformity among the various techniques currently used. In fact, the nature of the techniques is such that even with respect to each individual test, uniformity is difficult to maintain. For example, since the cellular suspension is placed in petri dishes and then subjected to irradiation in the various methods, uniformity can only be maintained if the distance between the cellular suspension and the light source is kept constant. Of course, it is rather evident that such distance depends upon the amount of cellular suspension placed in the petri dish and, clearly, the amount of cellular suspension in a petri dish can be a difficult factor to keep constant. Cells which are placed and suspended in a given volume of solution begin to settle to the bottom of the petri dish over time. Thus, the number of cells in suspension during irradiation tends to decrease throughout the irradiation process.

A related problem that arises when the cellular suspension is irradiated in petri dishes according to the above procedures is that it is difficult to subject all of the cells in the cellular suspension to the same amount of ultraviolet irradiation. That is due in part to the fact that the cellular suspension is somewhat stagnant in the petri dishes. That is to say, the cells in the suspension do not move throughout the suspension but rather, maintain their relative positions within the suspension. As a consequence, cells on the surface of the cellular suspension located closer to the ultraviolet light source are subjected to a different amount of irradiation than underlying cells in the cellular suspension. Although one of the foregoing articles mentions shaking the petri dish during irradiation, that technique would not be entirely effective in overcoming the aforementioned problem.

For example, shaking a petri dish that is not covered in order to subject the cells to movement results in an increase in the amount of evaporation of the cellular suspension. On the other hand, covering the petri dish prior to shaking may not be an effective solution because the material from which the cover is made can affect, and significantly reduce, the amount of irradiation received by the cellular suspension. Thus, a difficult calibration procedure is necessary.

Another drawback associated with the techniques currently employed in ultraviolet light irradiation for transplant/transfusion related procedures is that there is no stability with respect to other factors affecting the irradiation process. For instance, the temperature in the area surrounding the irradiation process can have a significant effect upon the intensity of the irradiation process. Accordingly, if the ambient temperature is not maintained at a particular level, consistent and reliable results will not be possible with respect to successive irradiation processes.

Similarly, during the initial hours of operation, the output from the ultraviolet light source can vary in fluorescent lamp systems. Thus, a cellular suspension irradiated during the initial hours of operation will be subjected to a different amount of irradiation than cellular suspensions that are irradiated later.

OBJECTS AND SUMMARY OF THE INVENTION

As can be seen from the foregoing discussion, a need exists for an apparatus and method for irradiating cells that can overcome the drawbacks associated with the techniques presently employed. It is, therefore, an object of the present invention to provide an apparatus and method for irradiating cells with ultraviolet light that permits uniformity with respect to the manner in which the cells in the cellular suspension are irradiated.

It is also an object of the present invention to provide an apparatus and method for irradiating cells with ultraviolet light that permits stability with respect to the operation of the apparatus. Providing an apparatus and method that can meet the two foregoing objectives is desirable because after the apparatus has been calibrated to ensure that the cells in a particular amount of cellular suspension will be subjected to a particular amount of ultraviolet irradiation in a given amount of time, one can be assured that subsequent operations of the apparatus will provide substantially the same results as those expected from the calibration of the apparatus.

It is an additional object of the present invention to provide an apparatus and method for irradiating cells that is relatively simple and inexpensive to manufacture, and relatively easy to operate.

It is a further object of the present invention to provide an apparatus and method for irradiating cells that is able to inhibit the transmission of ultraviolet light having a particular wavelength so that the cells in the cellular suspension are not subjected to such ultraviolet light. In that way, the potentially harmful effects of ultraviolet light having a particular wavelength can be avoided.

Those and other objects that will become more apparent from the following description, including the appended claims and the drawings, are achieved through the apparatus and method according to the present invention.

The apparatus includes an ultraviolet light source and an outer cylinder that surrounds the ultraviolet light source. An arrangement is provided for carrying suspended cells that are to be subjected to ultraviolet irradiation. Preferably, that arrangement includes hollow tubing that is wrapped helically around the outer peripheral surface of the outer cylinder.

In addition to the above features, the apparatus can also include an inner cylinder that is positioned between the outer cylinder and the ultraviolet light source. The apparatus can include an arrangement for filtering the ultraviolet light so that ultraviolet light having a particular wavelength is inhibited from passing through the inner and/or outer cylinders. Also, the apparatus can include an arrangement for ventilating the system in order to maintain a substantially constant temperature.

The method for irradiating potential transplant cells with ultraviolet light according to the present invention includes the steps of feeding a cell suspension into an inlet end of a transport arrangement for transporting and guiding the cell suspension, transporting the cell suspension over at least a portion of an outer surface of an outer cylinder, irradiating the suspended cells with ultraviolet light from an ultraviolet light source that is positioned inside the outer cylinder and collecting the cell suspension after irradiation in a collection reservoir as the cell suspension exits an outlet of the transport arrangement.

BRIEF DESCRIPTION OF THE DRAWINGS

A preferred embodiment of the present invention will be described in greater detail with reference to the accompanying drawings, wherein like elements bear like reference numerals and where:

FIG. 1 is a front view of the apparatus for irradiating cells according to a preferred embodiment of the present invention;

FIG. 2 is a cross-sectional view of a preferred embodiment of an apparatus according to the present invention taken along the sectional line 2—2 in FIG. 1;

FIG. 3 is a cross-sectional view of a preferred embodiment of an apparatus according to the present invention taken along the sectional line 3—3 in FIG. 2;

DETAILED DESCRIPTION OF THE PREFERRED EMBODIMENT

Figure 4:
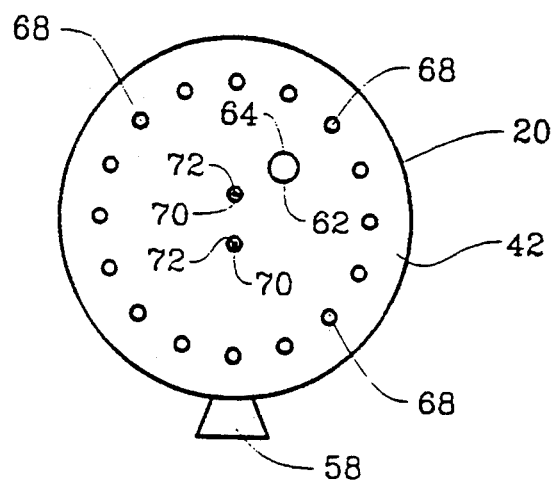
FIG. 4 is a right end view of a preferred embodiment of an apparatus according to the present invention.

Referring initially to FIG. 1, the apparatus 20 for irradiating cells includes a hollow outer cylinder 22 that extends in a longitudinal direction. Hollow tubing 24 is wrapped helically around the outer peripheral surface of the outer cylinder 22. The helically wrapped tubing 24 extends along substantially the entire longitudinal extent of the outer cylinder 22. It will be noted that in the preferred embodiment, the tubing 24 is wound around the outer peripheral surface of the first cylinder 22 in such a manner that each successive wrap of the tubing 24 closely abuts the previous wrap. Hence, a tight arrangement of the helically wound tubing 24 is obtained.

As seen in FIG. 2, a hollow inner cylinder 26 is positioned inside the outer cylinder 22. The inner cylinder 26 also extends in the longitudinal direction and is substantially parallel to the outer cylinder 22. The inner cylinder 26 is spaced from the outer cylinder 22 so that a space 28 exists between the inner surface 30 of the outer cylinder 22 and the outer surface 32 of the inner cylinder 26.

Located centrally in the apparatus 20 is an ultraviolet light source 34. The ultraviolet light source 34 also extends in the longitudinal direction and is substantially parallel to the outer cylinder 22 and the inner cylinder 26. Thus, both the outer cylinder 22 and the inner cylinder 26 surround the ultraviolet light source 34. The ultraviolet light source 34 is spaced from the inner cylinder 26 so that a space 36 exists between the inner surface 38 of the inner cylinder 26 and the outer surface 40 of the ultraviolet light source 34. The ultraviolet light source 34, the inner cylinder 26 and the outer cylinder 22 are all of substantially the same length.

Turning to FIG. 3, the apparatus 20 further includes a first seal member 42 and a second seal member 44. The first seal member 42 serves to seal the first end 46 of the outer cylinder 22 while the second seal member 44 serves to seal the second end 48 of the outer cylinder 22. The first seal member 42 is positioned with respect to the outer cylinder 22 such that the end face at the first end 46 of the outer cylinder 22 abuts against the inner surface 50 of the first seal member 42. Similarly, the second seal member 44 is positioned with respect to the outer cylinder 22 such that the inner surface 52 of the second seal member 44 abuts against the end face of the outer cylinder 22 that is located at the second end 48 of the outer cylinder 22.

It can be further seen from FIG. 3 that the inner cylinder 26 is substantially the same length as the outer cylinder 22. Accordingly, the inner face 50 of the first seal member 42 abuts against the end face of the inner cylinder 26 that is located at the first end 54 of the inner cylinder 26. Likewise, the end face of the inner cylinder 26 located at the second end 56 of the inner cylinder 26 abuts against the inner surface 52 of the second seal member 44.

Supporting members 58 are integrally connected to each of the seal members 42, 44. The supporting members 58 serve the purpose of supporting the apparatus 20 in a horizontal manner on a horizontal surface. It is, of course, understood that some other form of support can be provided as an alternative to the supporting members 58.

With continued reference to FIG. 3, at least one and preferably a plurality of spaced apart apertures 60 extend radially through the inner cylinder 26. The apertures 60 are positioned adjacent the second end 56 of the inner cylinder 26 and, preferably, the apertures 60 extend around the entire circumference of the inner cylinder 26. As a result of the abutting arrangement of the first and second seal members 42, 44 with respect to the inner and outer cylinders 26, 22, and the presence of the apertures 60 extending through the inner cylinder 26, the space 28 between the inner and outer cylinders 26, 22 is in fluid communication with the space 36 between the inner cylinder 26 and the light source 34.

The first seal member 42 as seen in FIG. 4 includes preferably one first hole 62 that extends through the first seal member 42 and that is positioned in such a manner as to communicate the space 36 between the inner surface 38 of the inner cylinder 26 and the outer surface 40 of the ultraviolet light source 34 with the atmosphere. As a result of the abutting arrangement of the first seal member 42 and the inner and outer cylinders 26, 22, the hole 62 can communicate with the space 36 between the inner cylinder 26 and the light source 34 and the space 28 between the inner and outer cylinders 26, 22 through the previously described apertures 60. Positioned in the first hole 62 is an inlet port 64. The inlet port 64 is adapted to be connected to a suitable source of air 66 such as a small duct fan. According to that arrangement, the duct fan can blow or suction air through the inlet port 64 and into the space 36 through the radially positioned apertures 60.

The first seal member 42 also includes at least one and preferably a plurality of second holes 68 that extend through the first seal member 42. The second holes 68 are positioned such that the space 28 between the inner surface of the outer cylinder 30 and the outer surface 32 of the inner cylinder 26 is in communication with the atmosphere. Once again, since the first seal member 42 is in abutting relation to the inner and outer cylinders 26, 22, the plurality of second holes 68 can only communicate with the space 28.

Figure 5:
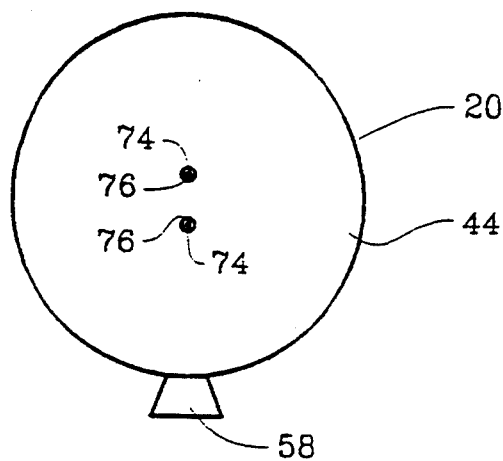
FIG. 5 is a left end view of a preferred embodiment of an apparatus according to the present invention therefor.

The first seal member 42 further includes two additional holes 70 through which the tube pins 72 extending from one end of the ultraviolet light source 34 can extend. As can be seen in FIG. 5, the second seal member 44 also includes two holes 74 through which the two tube pins 76 extending from the other end of the ultraviolet light source 34 can extend. In that way, a suitable power source (not shown) can be connected to the tube pins 72, 76 in order to provide power to the ultraviolet light source 34.

Turning once again to FIG. 1, one end of the helically wound tube 24, the inlet end, is connected to a suitable container 78 in which is located the cellular suspension that is to be subjected to irradiation by the ultraviolet light source 34. The container 78 can be either a transfusion bag or some other type of sterile container that is equipped to filter incoming air, if needed. A variable rate pump 80 is also provided at the inlet end of the helically wound tube 24. The variable rate pump 80 serves to move the cell suspension located in the container 78 through the helically wound tube 24.

A collection reservoir 82 is connected to the opposite end of the helically wound tubing, the outlet end, in order to permit collection of the cellular suspension that has been irradiated by the ultraviolet light source 34.

The outer cylinder 22 and the inner cylinder 26 should be manufactured from materials that are well suited for transmitting and filtering ultraviolet light. The material from which the inner and outer cylinders 26, 22 are manufactured should be capable of transmitting at least ninety percent of the preferred ultraviolet light spectrum. One material that has been found to give desirable results is fused silicate glass. That material offers certain advantages over other materials, such as, for example, optical grade plastic, in that the fused silicate glass possesses greater stability under temperature changes. It should be understood, however, that materials other than fused silicate quartz can be employed so long as the material selected is capable of performing the intended objective.

For the most part, fluorescent ultraviolet lamp systems emit a combination of U.V.-A, U.V.-B, and U.V.-C light and differ in their spectral distribution and intensity. For example, a U.V.-B tube emits mostly U.V.-B light that falls between 280 and 320 nanometers. The same tube, however, also emits to some extent a minimal amount of U.V.-A and U.V.-C light.

Preferably, the ultraviolet light source 34 used in the present invention is a U.V.-B medium wave fluorescent tube. Such a tube is suitable because, as mentioned above, it emits an optimal distribution of ultraviolet light within a range of approximately 280 nanometers (nm) to 320 nanometers (nm). That range of ultraviolet light has been found to be most suitable for irradiating potential transplant cells in a cellular suspension. However, as was pointed out previously, the U.V.-B medium wave fluorescent tube emits minimal but additional amounts of ultraviolet light over a range of wavelengths outside the 280–320 nanometer range. Ultraviolet light ouside the 280–320 nanometer range has been found to be not entirely suitable for irradiating potential transplant cells.

In order to address that concern, a filtering arrangement can be provided with respect to the inner and/or outer cylinders in order to inhibit the transmission of ultraviolet light having the undesired wavelength. The use of an ultraviolet light source that is capable of emitting ultraviolet light having the desired spectral distribution and range is particularly well adapted to be used in conjunction with a filtering arrangement because the filtering arrangement would permit the portion of the ultraviolet light having the desired wavelength to pass through the inner and outer cylinders while also allowing the undesirable and potentially harmful portion of the ultraviolet light outside of the U.V.-B range to be filtered prior to reaching the helically wound tube and the cellular suspension contained therein.

One portion of the spectral range of ultraviolet light that has been found to be undesirable is ultraviolet light in the U.V.-C range. It has been determined that ultraviolet light in the U.V.-C range is not particularly well suited for irradiating cells because of its high energy and short wavelength properties.

Figure 6:
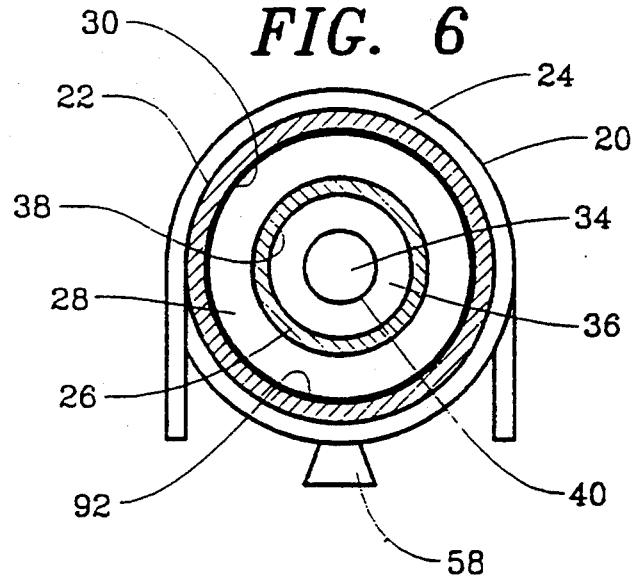
FIG. 6 is a cross-sectional view similar to FIG. 2 except illustrating a different placement for the filter.

In one embodiment, the above-described filtering arrangement can take the form of a film that is coated on the outer surface 32 of the inner cylinder 26. One film that has been found to be particularly well suited for inhibiting or blocking the transmission of high energy, short wavelength U.V.-C light is "KODACEL" TA 401 film manufactured by the Eastman Kodak Co. It is preferable that the film be capable of inhibiting the transmission of U.V.-C light having a wavelength in the range between approximately 200 nanometers and 280 nanometers. While the aforementioned film is preferably positioned on the outer peripheral surface 32 of the inner cylinder 26, (see reference numeral 90, FIG. 2) it may be desirable to coat the inner surface 30 of the outer cylinder 22 with the same type of film (see reference numeral 92, FIG. 6). However, in order to maximize the stability of the film, the filters are preferably placed away from the ultraviolet light source. A film coating having a thickness of between 0.10 mm and 0.15 mm has been found to provide desirable results although other thicknesses could be utilized depending upon the results desired.

While it is desirable that the high energy, short wavelength U.V.-C light be filtered in the aforementioned manner in order to avoid irradiation of the cellular suspension by that portion of the ultraviolet light, filtering and inhibiting the transmission of U.V.-A light is not quite as great a concern. That is because the U.V.-A light is a low energy, long wavelength range of light. As a result, the U.V.-A light will not have the same potentially harmful effects on the cellular suspension as the high energy, short wavelength U.V.-C light.

Nevertheless, in order to ensure that the cellular suspension is subjected to only U.V.-B light, a filtering arrangement can be provided for inhibiting the transmission of U.V.-A light through the inner and/or outer cylinders 26, 22. One particular filtering arrangement that has been found to be effective is the use of a nickel and cobalt sulfate filter which can be positioned in the aforementioned places in order to filter U.V.-A light and still transmit U.V.-B light. As an alternative, optical filters of any suitable type can be used so long as the optical filter is capable of achieving the desired objective of filtering the portion of the ultraviolet light with which the cellular suspension should not be irradiated. Also, anti-reflective coatings can be placed on the inner and/or outer cylinders to improve the transmission of ultraviolet light through the inner and/or outer cylinders.

It is to be understood from the foregoing that a filtering arrangement can be employed for inhibiting and blocking the transmission of U.V.-A light and U.V.-C light while permitting the transmission of U.V.-B light. Further, through the appropriate selection of films and/or optical filters, only the U.V.-B light having a desired wavelength can be permitted to irradiate the cellular suspension flowing in the tube 24.

The aforementioned filtering arrangement could also be utilized in conjunction with a different ultraviolet light source than that described above. For example, it may be desirable for other reasons to employ an ultraviolet light source that emits primarily U.V.-A light, primarily U.V.-C light or a combination of both.

The helically wound hollow tube 24 should preferably be manufactured from material that is adapted to readily transmit ultraviolet light. One type of material that has been found to be well suited for transmitting ultraviolet light is polypropylene. "EXTREL" polypropylene, and more specifically EX-50 polypropylene, manufactured by Exxon Chemical Co. has been determined to be desirable.

One of the advantages associated with the apparatus according to the present invention is that the apparatus 20 is equipped with a ventilation system that is designed to maintain a constant temperature in the apparatus 20 while the apparatus is in use. Turning to FIG. 3, the ventilation system operates in the following manner. The small duct fan 66, or other suitable source of air, blows air through the inlet port 64 and into the space 36 between the inner surface 38 of the inner cylinder 26 and the outer surface 40 of the ultraviolet lamp 34. The air is forced toward the second end 56 of the inner cylinder 26, whereupon the air flows through the plurality of apertures 60 that extend through the second cylinder 26. The air then flows, as illustrated by arrows A, toward the holes 68 that extend through the first seal member 42. It can be seen, therefore, that the continuous flow of air from the duct fan 66 or other suitable source of air into the space 36, through the holes 60, through the space 28 and out the apertures 68 provides continuous ventilation of the apparatus 20 and ensures that the air in the closed system is continuously ventilated.

One of the advantages resulting from the ventilation system according to the present invention is evident when considered in light of the fact that changes in the ambient temperature can result in up to a sixty percent variation in the output of the ultraviolet lamp. If the apparatus is initially calibrated based upon results obtained when the apparatus is operated in a particular set of ambient conditions, the later operation of the apparatus at ambient conditions that are different from those that existed when the apparatus was first calibrated will result in the cellular suspension being irradiated by an amount that is at variance with the expected amount. Thus, the utilization of a ventilating system that helps ensure that the temperature in the apparatus is maintained at a substantially constant level will help ensure that the cells in the cellular suspension are irradiated at a desired level and by a desired amount of ultraviolet light.

It is to be understood that as an alternative to the duct fan 66, a vacuum or suction pump could be connected to the inlet port 64 in order to continuously ventilate the closed system. In that alternative arrangement, the vacuum pump would draw air into the space 28 through the holes 68 and the air would flow through the apertures 60 that extend through the inner cylinder 26, through the space 36 and out the port 64.

Another advantage associated with the ventilation system of the present invention concerns the aforementioned use of filters and the like for filtering and inhibiting the transmission of ultraviolet light having a particular wavelength. In that regard, the heat produced by the ultraviolet light source and the resulting temperature in the apparatus 20 can cause the filter surface to warp or shift. Through use of the ventilation system, the temperature within the apparatus 20 can be maintained at a level that is not harmful to the filter surface. To further enhance filter stability, the ventilating holes 68 that vent air between the outside air and the space 28 between the inner and outer cylinders 22, 26 can be switched with the inlet port 62 if so desired. Also, reverse air flow through use of the aforementioned vacuum or suction pump can transfer heat faster from the inner and outer cylinders to thereby avoid damaging the filter surfaces. That reverse air flow allows the heat generated by the lamp to leave the system faster because the heat is transferred immediately out of the system instead of being carried through it.

The variable rate pump 80 could be replaced with other devices that are adapted to perform a similar function. For example, a Harvard variable syringe pump or any type of adjustable high pressure pumping device could be employed for pumping the cellular suspension from the container 78 through the helically wound tube 24 and to the collection reservoir 82.

The use of an outer cylinder having an outer radius of approximately 24 mm and a length of approximately 190 mm as measured between the first and second seal members 42, 44 in conjunction with hollow tubing 24 having an inside diameter of approximately 1.02 mm and an outside diameter of 2.16 mm will permit approximately 10.84 ml of cellular suspension to be located in the tubing 24 over the exposure area of the apparatus. The outer radius of the inner cylinder 26 can be approximately 16 mm. Also, the spacing between the inner and outer cylinders 20, 22 and the spacing between the inner cylinder and the ultraviolet light source can be approximately 8 mm. Those dimensions and values are given only by way of example and are only intended to illustrate the fact that it is necessary to know the dimensions of the outer cylinder and the tubing so that the amount of cellular suspension contained in the tubing can be determined for dose calculation purposes, for calibration purposes, and for purposes of obtaining consistent results.

In order to ensure that the cells in the cellular suspension which are pumped through the helically wound tubing are irradiated by a known or determinable amount of ultraviolet light, it is important, and also essential, that the apparatus 20 be calibrated. As a first step in the calibration procedure, the ultraviolet tube or lamp 34 is burned continuously for approximately 100 hours. It has been found that the output of ultraviolet lamps fluctuates greatly during the initial hours of operation of the lamp. Accordingly, by letting the lamp burn continuously for 100 hours, the lamp's fluctuation in output can be reduced and substantially eliminated.

After the ultraviolet light has been continuously burned for approximately 100 hours, it is necessary to measure the output of the ultraviolet lamp. For that purpose, an integrating sphere and a spectral radiometer can be employed and as a result, the separate and total outputs of U.V.-A light, U.V.-B light and U.V.-C light can be determined. During measurement of the output of the ultraviolet lamp 34, the temperature in the apparatus should be maintained at a substantially constant value through operation of the aforementioned ventilation system.

Measurements taken with a narrow band detector or sensor and a lab radiometer can be standardized to the calibrated measurements and used at a later time to determine the amount of fluctuation in the apparatus 20 after, say, 6–8 months of use. As an example, say the calibrated measurements taken from the irradiating system output is initially 3.0 watts/square meter/second (W/m$^2$/s), using a narrow band detector and lab radiometer, the output reading can be standardized to the calibrated measurements. A reading from the lab radiometer reading 0.10 W/m$^2$/s would represent 100 percent of the irradiating system's output. If, say in six months the lab radiometer read 0.08 W/m$^2$/s, then the system output would be approximately 2.4 W/m$^2$/s or 80 percent of the initial operating output.

Using calibrated irradiation measurements, the total output of U.V.-B light from the ultraviolet light source can be obtained. That output, in watts per second, can be converted into watts per square meter per second by dividing by the surface area of the outer cylinder or, in other words, the exposure area. It can be seen that the exposure area of the apparatus can be increased by utilizing an outer cylinder having a larger diameter. The addition of a layer of film such as the "KODACEL" TA 401 film mentioned above at a maximum thickness of 0.15 mm will sufficiently filter out unwanted U.V.-C light. Increasing or doubling the maximum thickness would decrease by approximately 50 percent the amount of U.V.-B light that is transmitted through the cylinders and to the cells in the helically wound tubing 24. Also, the amount of irradiation can be further reduced by controlling the amount of current supplied to the ultraviolet lamp. An interfaced rheostat or variable power source can be employed for effecting such a reduction in irradiation.

By knowing that the following relationships exist, the pump rate necessary for effecting a particular irradiation of the cells in the cellular suspension can be determined.

dose (J/m$^2$) = irradiance (W/m$^2$/s) × time(s); where irradiance is measured after the aplication of any filters and after the output of the lamp has been reduced, if at all $$V \text{ (ml)} = \frac{\text{number of cells needed for transplant}}{\text{number of cells/ml of cell suspension}}$$

where $V$ = volume of cell suspension needed $$\text{pump rate (ml/min)} = \frac{V \text{ (ml)}}{\text{time(s)}}$$

By way of example, it has been determined that in a typical bone marrow transplant, the concentration of cells needed to rescue an allogeneic recipient is approximately $2.3 \times 10^9$ cells for 10 rats. Through use of an outer cylinder and inner cylinder having the dimensions noted above, utilizing a second 0.15 mm coating of "KODACEL" TA 401 on the outer surface of the inner cylinder (which further reduces the output of the ultraviolet lamp by 50 percent), adjusting the power to the ultraviolet lamp to thirty percent and having determined that the appropriate dose is approximately 150 J/m$^2$, it can be determined from the foregoing relationships that the appropriate pumping rate should be approximately 2.26 ml/min. when the cell concentration is about $2.3 \times 10^8$ cells/ml.

Having determined the appropriate pumping rate, the variable rate pump 80 or other suitable device is set to that rate and the cellular suspension in the container 78 is permitted to flow into the inlet end of the tubing 24. Through the pumping action of the pump 80, the cellular suspension is fed through the tubing 24 and over the exposure area where the cells in the cellular suspension are irradiated by the ultraviolet light source. The cellular suspension flows along the length of the tubing and over the entire exposure area so as to be subjected to the previously determined appropriate dosage of ultraviolet light irradiation. The irradiated cells in the cellular suspension exit the tubing 24 at the outlet end and are collected in the collection reservoir 82. The cells are then transplanted into the recipient.

Although the foregoing description of the apparatus and method according to the present invention has been described in terms of being used in conjunction with bone marrow transplants, it is to be understood that the apparatus and method could also be employed in other cellular transplant and transfusion related procedures. Further it should be understood that other cylinders in addition to the inner and outer cylinders described above could be employed.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others without departing from the spirit of the present invention. Accordingly, it is expressly intended that all such variations and changes which fall within the spirit and scope of the present invention as defined in the claims be embraced thereby.

What is claimed is:

1. A method of irradiating potential transplant cells with ultraviolet light through use of an apparatus comprising the steps of:
    feeding a cell suspension into an inlet end of a transport means for transporting and guiding the cell suspension;
    transporting and guiding the cell suspension over at least a portion of an outer peripheral surface of an outer cylinder;
    irradiating the suspended cells with ultraviolet light from an ultraviolet light source that is positioned inside the outer cylinder;
    ventilating the apparatus by blowing air into a space located between an outer surface of the ultraviolet light source and an inner surface of an inner cylinder positioned between the outer cylinder and the ultraviolet light source, permitting the air to flow into a space located between an inner surface of the outer cylinder and outer surface of the inner cylinder, and permitting the air to exit the apparatus; and
    collecting the cell suspension after irradiation in a collection reservoir as the cell suspension exits an outlet of the transport means.

2. The method in accordance with claim 1, further including the step of filtering the ultraviolet light from the ultraviolet light source so that the suspended cells are not irradiated by ultraviolet light having a wavelength less than about 280 nanometers.

3. The method in accordance with claim 1, wherein the step of irradiating the cells with ultraviolet light includes irradiating the cells with ultraviolet light having a wavelength not less than about 280 nanometers.

4. A method of irradiating potential transplant cells with ultraviolet light through use of an apparatus in order to alter antigen expression and recognition of the cells comprising the steps of:
    feeding a cell suspension into an inlet end of a helically arranged transport means for transporting and guiding the cell suspension;
    helically transporting and guiding the cell suspension through the transport means over at least a portion of an outer peripheral surface of an outer cylinder, the cell suspension being transported and guided through the transport means which is separate from and encircles the outer peripheral surface of the outer cylinder;
    altering antigen expression and recognition of the cells by irradiating the suspended cells with ultraviolet light from an ultraviolet light source that is positioned inside the outer cylinder, said cells being irradiated with ultraviolet light having a wavelength not less than about 280 nanometers; and
    introducing the irradiated cells whose antigen expression and recognition has been altered into a living recipient.

5. The method in accordance with claim 4, wherein the ultraviolet light is filtered so that the cells are not subjected to ultraviolet light having a wavelength greater than about 320 nanometers.

6. The method in accordance with claim 4, and further including the step of ventilating the apparatus by blowing air into a space located between an outer surface of the ultraviolet light source and an inner surface of an inner cylinder positioned between the outer cylinder and the ultraviolet light source, permitting the air to flow into a space located between an inner surface of the outer cylinder and outer surface of the inner cylinder, and permitting the air to exit the apparatus.

7. The method in accordance with claim 4, wherein the ultraviolet light from the ultraviolet light source is filtered so that the suspended cells are irradiated with ultraviolet light having a wavelength not less than about 280 nanometers.

8. A method of irradiating potential transplant cells with ultraviolet light through use of an apparatus in order to alter antigen expression and recognition of the cells comprising the steps of:
    feeding a cell suspension into an inlet end of a helically arranged transport means for transporting and guiding the cell suspension;
    helically transporting and guiding the cell suspension through the transport means over at least a portion of an outer peripheral surface of an outer cylinder;
    altering antigen expression and recognition of the cells by irradiating the suspended cells with ultraviolet light from an ultraviolet light source positioned inside an inner cylinder which is disposed within and spaced from the outer cylinder, said cells being irradiated with ultraviolet light having a wavelength not less than about 280 nanometers; and
    introducing the irradiated cells whose antigen expression and recognition has been altered into a living recipient.

9. The method in accordance with claim 8, further including the steps of permitting the ultraviolet light source to burn for a predetermined continuous period of time prior to feeding the cell suspension into the transport means in order to stabilize the intensity and output of the ultraviolet light source and to permit calibration of the apparatus.

10. The method in accordance with claim 8, wherein said step of irradiating the cells includes irradiating the cells with ultraviolet light having a wavelength not greater than about 320 nanometers.

11. A method of inducing alteration of antigen expression and recognition of cells, comprising:
providing cells from a donor source;
subjecting said cells to ultraviolet radiation while said cells are being conveyed through a helically arranged conveying means to alter antigen expression and recognition of the cells to the extent necessary to change immune response to the cells, said cells being subjected to ultraviolet irradiation by subjecting the cells to ultraviolet light having a wavelength not less than 280 nanometers, said cells being conveyed in a helical path through the conveying means which is separate from and encircles an outer peripheral surface of an outer cylinder; and
introducing into a living recipient the cells whose antigen expression has been altered through ultraviolet irradiation in order to modify antigen recognition of the transplanted cells and thereby change immune response in the living recipient.

12. The method according to claim 11, wherein said step of subjecting the cells to ultraviolet irradiation includes subjecting the cells to ultraviolet light that has been filtered to remove ultraviolet light having a wavelength greater than about 320 nanometers.

13. The method according to claim 11, wherein said step of subjecting the cells to ultraviolet irradiation includes subjecting the cells to ultraviolet light that has been filtered to remove ultraviolet light having a wavelength less than about 280 nanometers.

14. A method of inducing alteration of antigen expression and recognition of cells, comprising:
providing cells from a donor source;
subjecting said cells to ultraviolet radiation while said cells are being conveyed through conveying means to alter antigen expression and recognition to the extent necessary to change immune response to the cells, said cells being subjected to ultraviolet irradiation by subjecting the cells to ultraviolet light having a wavelength not less than 280 nanometers, the cells being conveyed through conveying means positioned exteriorly of an outer cylinder and being subjected to ultraviolet radiation from an ultraviolet radiation source positioned inside an inner cylinder which is disposed within and spaced from the outer cylinder; and
introducing into a living recipient the cells whose antigen expression has been altered through ultraviolet irradiation in order to modify antigen recognition of the transplanted cells and thereby change immune response in the living recipient.

15. The method according to claim 14, wherein said conveying of the cells through conveying means includes conveying the cells through helically wound tubing while being subjected to the ultraviolet irradiation.

16. The method in accordance with claim 14, wherein said step of irradiating the cells includes irradiating the cells with ultraviolet light having a wavelength not greater than about 320 nanometers.

* * * * *